US00PP28797P3

(12) United States Plant Patent
van den Hoogen

(10) Patent No.: US PP28,797 P3
(45) Date of Patent: Dec. 26, 2017

(54) ***VERONICA* PLANT NAMED 'ALLKISS'**

(50) Latin Name: *Veronica longifolia*
Varietal Denomination: Allkiss

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 70 days.

(21) Appl. No.: 14/998,860

(22) Filed: Feb. 23, 2016

(65) Prior Publication Data

US 2017/0245409 P1 Aug. 24, 2017

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

UPOV hit on *Veronica* plant named 'Allkiss', QZ PBR 20152095, published Dec. 15, 2015.*

* cited by examiner

*Primary Examiner* — Anne Grunberg
(74) *Attorney, Agent, or Firm* — C. A. Whealy

(57) ABSTRACT

A new and distinct cultivar of *Veronica* plant named 'Allkiss', characterized by its upright plant habit; freely flowering habit; dense inflorescences with numerous pink-colored flowers; long flowering period; and suitable as a cut flower or container plant.

2 Drawing Sheets

Botanical designation: *Veronica longifolia.*
Cultivar denomination: 'ALLKISS'.

BACKGROUND OF THE INVENTION

The present invention relates to a new and distinct cultivar of *Veronica* plant, botanically known as *Veronica longifolia* and hereinafter referred to by the name 'Allkiss'.

The new *Veronica* plant is a product of a planned breeding program conducted by the Inventor in Cuijk, The Netherlands. The objective of the breeding program is to create new attractive *Veronica* plants that can be used as a cut flower or container plant.

The new *Veronica* plant originated from an open-pollination in September, 2012 of a proprietary selection of *Veronica longifolia* identified as code number 11-24-1, not patented, as the female, or seed, parent with an unknown selection of *Veronica longifolia* as the male, or pollen, parent. The new *Veronica* plant was discovered and selected by the Inventor as a single flowering plant from within the progeny of the stated open-pollination in a controlled environment in Cuijk, The Netherlands in September, 2013.

Asexual reproduction of the new *Veronica* plant by vegetative cuttings in a controlled environment in Cuijk, The Netherlands, since March, 2015 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allkiss'. These characteristics in combination distinguish 'Allkiss' as a new and distinct *Veronica* plant:

1. Upright plant habit.
2. Freely flowering habit.
3. Dense inflorescences with numerous pink-colored flowers.
4. Long flowering period.
5. Suitable as a cut flower or container plant.

Plants of the new *Veronica* differ primarily from plants of the female parent selection in the following characteristics:

1. Plants of the new *Veronica* are more freely flowering than plants of the female parent selection.
2. Plants of the new *Veronica* have broader inflorescences than plants of the female parent selection.
3. Flowers of plants of the new *Veronica* are darker pink in color than flowers of plants of the female parent selection.

Plants of the new *Veronica* can be compared to plants of *Veronica longifolia* 'Alllove', disclosed in U.S. Plant Pat. No. 21,478. In side-by-side comparisons conducted in Cuijk, The Netherlands, plants of the new *Veronica* differ primarily from plants of 'Alllove' in the following characteristics:

1. Leaves of plants of the new *Veronica* are longer and narrower than leaves of plants of 'Alllove'.
2. Inflorescences of plants of the new *Veronica* are longer than inflorescences of 'Alllove'.

3. Plants of the new *Veronica* are more freely flowering than plants of 'Alllove'.
4. Plants of the new *Veronica* and 'Alllove' differ in flower color as plants of 'Alllove' have intense red purple-colored flowers.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Allkiss'.

The photograph at the top of the second sheet is a close-up view of typical inflorescences of 'Allkiss'.

The photograph at the bottom of the second sheet is a close-up view of the upper surface of a typical leaf of 'Allkiss'.

DETAILED BOTANICAL DESCRIPTION

Plants used for the aforementioned photographs and following description were grown during the summer in ground beds in an outdoor nursery in Rijswijk, The Netherlands and under cultural practices typical of commercial *Veronica* production. During the production of the plants, day temperatures ranged from 16° C. to 30° C. and night temperatures ranged from 6° C. to 18° C. Plants were 27 weeks old when the photographs and the description were taken. In the following description, color references are made to The Royal Horticultural Society Colour Chart, 2015 Edition, except where general terms of ordinary dictionary significance are used.

Botanical classification: *Veronica longifolia* 'Allkiss'.

Parentage:

*Female, or seed, parent*.—Proprietary selection of *Veronica longifolia* identified as code number 11-24-1, not patented.

*Male, or pollen, parent*.—Unknown selection of *Veronica longifolia*, not patented.

Propagation:

*Type cutting*.—Vegetative cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial.

*Plant and growth habit*.—Narrowly upright inverted triangle; freely basal branching habit with about four main stems each with about six lateral branches; moderately vigorous growth habit.

*Plant height*.—About 58.5 cm.

*Plant width*.—About 38.8 cm.

*Lateral branch description*.—Length: About 17 cm. Diameter: About 3 mm. Internode length: About 5.5 cm. Strength: Strong. Aspect: Main stems, mostly upright; lateral branches, about 35° from main stem. Texture and luster: Densely pubescent; matte. Color: Close to 143B.

Leaf description:

*Arrangement*.—Opposite, simple.

*Length*.—About 8.1 cm.

*Width*.—About 3.9 cm.

*Shape*.—Ovate to narrowly ovate; slightly carinate.

*Apex*.—Bluntly acute.

*Base*.—Truncate.

*Margin*.—Serrate.

*Texture and luster, upper surface*.—Sparsely pubescent; very slightly glossy.

*Texture and luster, lower surface*.—Moderately pubescent; matte.

*Venation pattern*.—Pinnate.

*Color*.—Developing leaves, upper surface: Close to 137B. Developing leaves, lower surface: Close to 146B. Fully expanded leaves, upper surface: Close to NN137A; venation, close to 147C. Fully expanded leaves, lower surface: Close to between 146B and 147B; venation, close to 144A.

*Petioles*.—Length: About 1.6 cm. Diameter: About 2 mm by 2.5 mm. Texture, upper and lower surfaces: Smooth. Color, upper surface: Close to 143B. Color, lower surface: Close to 143C.

Flower description:

*Flower arrangement and shape*.—Single campanulate flowers arranged on dense terminal and axillary racemes; flowers face mostly outwardly.

*Flowering habit*.—Freely flowering habit with about 500 flowers developing per inflorescence and more than 10,000 flowers developing per plant during the flowering season.

*Fragrance*.—None detected.

*Natural flowering season*.—Long flowering period; plants flower continuously from mid-June to late September in The Netherlands.

*Flower longevity as a cut flower*.—About ten days; flowers persistent.

*Flower longevity on the plant*.—About 25 days; flowers persistent.

*Flower buds*.—Length: About 4 mm. Diameter: About 2 mm. Shape: Ovate. Color: Close to 62A.

*Inflorescence height*.—About 16.9 cm.

*Inflorescence diameter*.—About 1.8 cm.

*Flower diameter*.—About 3 mm.

*Flower height*.—About 5.5 mm.

*Petals*.—Quantity and arrangement: Four in a single whorl; petals fused about 50% of the length from the base. Length: About 5 mm. Width: About 2.5 mm. Shape: Obovate. Apex: Obtuse. Margin: Entire. Texture and luster, upper and lower surfaces: Smooth, glabrous; matte. Color: When opening, upper and lower surfaces: Close to 63C; towards the base, close to 63B. Fully opened, upper and lower surfaces: Close to 63C; color becoming closer to 63D and 65B to 65C with development.

*Sepals*.—Quantity and arrangement: Four in a single whorl; sepals fused about 25% of the length from the base. Length: About 1.25 mm to 2 mm. Width: About 1 mm. Shape: Narrowly ovate. Apex: Acute. Margin:

Entire. Texture, upper and lower surfaces: Smooth, glabrous. Color: When opening and fully opened, upper surface: Close to 137D. When opening and fully opened, lower surface: Close to 137C.

*Peduncles*.—Length: About 16.4 cm. Diameter: About 2 mm. Aspect: Mostly upright. Strength: Strong. Texture: Smooth, glabrous. Color: Close to 138B.

*Pedicels*.—Length: About 1 mm. Diameter: About 0.75 mm. Aspect: About 50° from peduncle axis. Strength: Strong. Texture: Smooth, glabrous. Color: Close to 137D.

*Reproductive organs*.—Stamens: Stamen development has not been observed on plants of the new *Veronica*. Pistils: Quantity per flower: One. Pistil length: About 4 mm. Stigma shape: Clavate. Stigma color: Close to 72A. Style length: About 3.75 mm. Style color: Close to 70B. Ovary color: Close to 144C.

*Seeds and fruits*.—Seed and fruit development has not been observed on plants of the new *Veronica*.

Disease & pest resistance: Plants of the new *Veronica* have not been noted to be resistant to pathogens and pests common to *Veronica* plants.

Garden performance: Plants of the new *Veronica* have exhibited good garden performance and to be tolerant to rain, wind, high temperatures about 35° C. and to be hardy to USDA Hardiness Zone 4.

It is claimed:

1. A new and distinct *Veronica* plant named 'Allkiss' as illustrated and described.

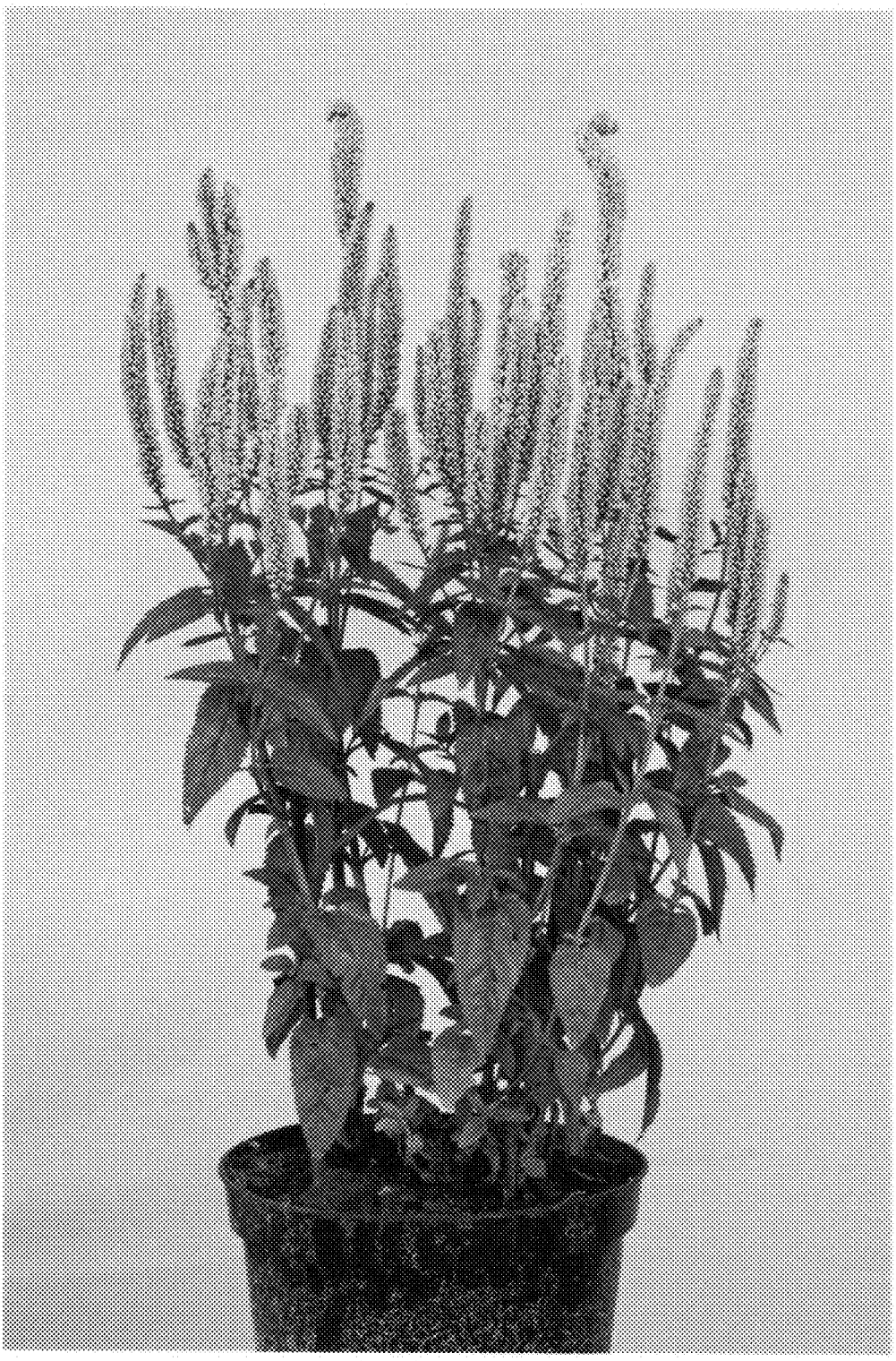

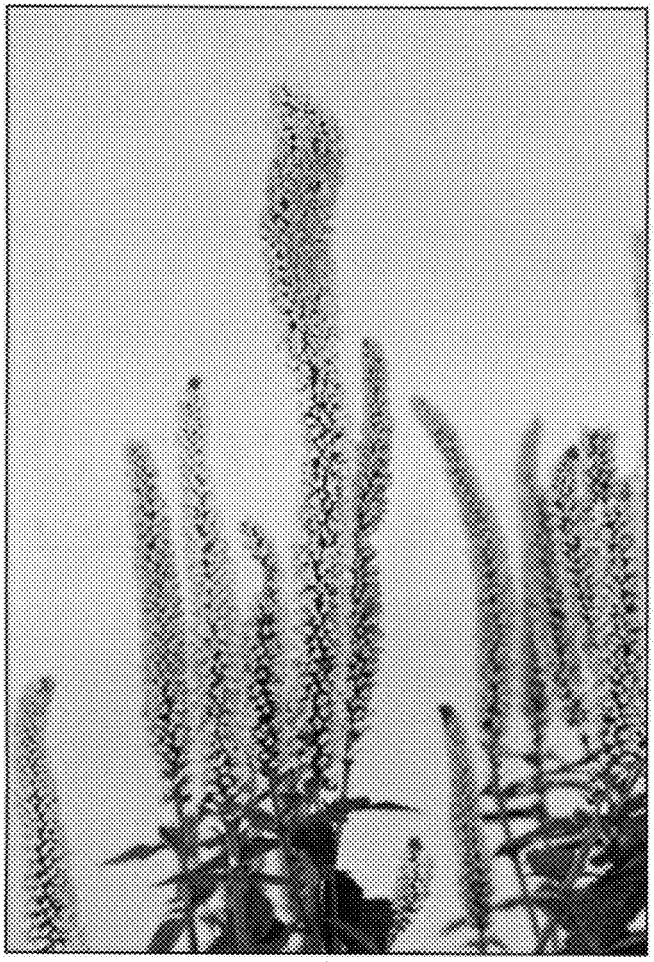
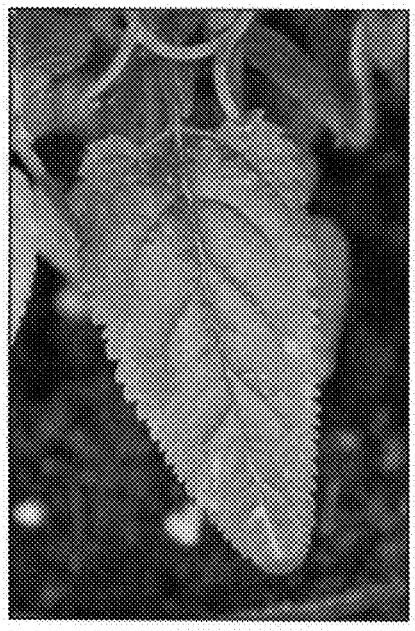

* * * * *